United States Patent [19]
Brasile

[11] Patent Number: 5,643,712
[45] Date of Patent: Jul. 1, 1997

[54] METHOD FOR TREATING AND RENDERING GRAFTS NONTHROMBOGENIC AND SUBSTANTIALLY NONIMMUNOGENIC USING AN EXTRACELLULAR MATRIX COATING

[76] Inventor: Lauren Brasile, 61 Meadow La., Albany, N.Y. 12208

[21] Appl. No.: 437,155

[22] Filed: May 17, 1995

Related U.S. Application Data

[63] Continuation-in-part of Ser. No. 246,803, May 20, 1994, abandoned.

[51] Int. Cl.$^6$ .................................. A01N 1/02; A61F 2/04
[52] U.S. Cl. ................................... 435/1.2; 600/36
[58] Field of Search .................... 435/1.2, 1.1; 424/422, 424/423, 572; 600/36

[56] References Cited

PUBLICATIONS

Lee YS et al, Asaio J. 39(3) M740–5 (1993).
Köveker GB, Surgery 109:313–319 (1991).

*Primary Examiner*—David M. Naff
*Assistant Examiner*—S. Saucier
*Attorney, Agent, or Firm*—Hodgson, Russ, Andrews, Woods & Goodyear

[57] ABSTRACT

The present invention is directed to methods and compositions for immunomodifying a graft so that it is nonthrombogenic and substantially nonimmunogenic when transplanted into a recipient. In an ex vivo process, the lumenal surfaces of blood vessels comprising the vasculature within the graft are coated with an extracellular matrix, or membrane synthesized therefrom, that renders the surface substantially nonimmunogenic and nonthrombogenic to the recipient, while maintaining the viability of the donor graft vascular endothelial cells remaining underneath the coating. In addition, the extracellular matrix may provide a surface, exposed to the lumen, that can support efficient re-endothelialization with vascular endothelial cells allogeneic or preferably autologous with respect to the recipient receiving the graft.

7 Claims, 2 Drawing Sheets

METHOD FOR TREATING AND RENDERING GRAFTS NONTHROMBOGENIC AND SUBSTANTIALLY NONIMMUNOGENIC USING AN EXTRACELLULAR MATRIX COATING

This is a continuation-in-part of application U.S. Ser. No. 08/246,803 filed on May 20, 1994, which is herein incorporated by reference, and which is now abandoned.

BACKGROUND OF THE INVENTION

1. Field of the Invention

This invention relates generally to a process of rendering an allograft or xenograft ("foreign graft") nonthrombogenic and substantially nonimmunogenic for transplantation purposes. More particularly, the process involves creating an ex vivo interface between donor and recipient by coating the vascular endothelial cells, lining the lumen of blood vessels within the vascular network of the graft, with endothelial extracellular matrix immunologically tolerable (i.e., tolerated as an autograft) to the recipient; thereby providing a substantially nonimmunogenic, nonthrombogenic interface which provides a surface that enhances the re-endothelialization of the graft with host/recipient endothelium in "immunomodifying" the graft.

2. Description of the Background and Related Art

Organ transplantation is the therapy of choice for end-stage organ failure. In the case of kidneys, transplantation provides for increased life expectancy, enhanced quality of life, and is more cost-effective than maintaining patients on hemodialysis. In the case of extrarenal organs, transplantation is life-saving since no equivalent to hemodialysis exists for these organs. The limiting factor today in the number of transplant procedures performed is the severe shortage of organs (Annual Report for the U.S. Scientific Registry for Organ Transplantation and the Organ Procurement and Transplantation Network, 1990).

To address organ shortage problems by providing ways in which organs/grafts can be better preserved for transplantation, a warm preservation technology (between 18° C. to 35° C.) was developed with others by the present inventors. U.S. patent application Ser. No. 08/029,459 discloses a method of warm preservation of a tissue intended for transplantation using a preservation solution that may be used for the initial flushing, and as a perfusate for storage of the tissue/organ (the disclosure of which is herein incorporated by reference). U.S. patent application Ser. No. 08/033,629 now abandoned discloses a method of warm preservation of a tissue intended for transplantation using a perfusate, supplemented with a perfluorochemical emulsion, for storage of the tissue/organ (the disclosure of which is herein incorporated by reference).

However, other problems need be addressed in the transplantation process. For example, without immunosuppressive agents/drugs, the onset of rejection of an anallograft may occur approximately seven days posttransplant. In the case of a xenograft, rejection may occur within a matter of minutes or hours. Rejection of the transplanted graft is an immunological assault in which the recipient's immune system recognizes the graft as "foreign" and attempts to eliminate the transplanted graft. The current theory of rejection in transplantation involves both the humoral and cell-mediated immune responses. The humoral response involves binding of the recipient's naturally occurring antibodies to the donor's vascular endothelial cells lining the blood vessels within the transplanted graft. Antibody deposition leads to the activation of the complement cascade which mediates a cytotoxic phenomenon which can directly damage or kill the endothelial cells. In addition the complement cascade leads to the activation of the endothelial cells which causes subsequent change in the anticoagulant environment. More specifically, the vascular endothelium normally provides a nonthrombogenic surface; therefore, when activated by the immune system during the rejection process, the endothelial lining transforms into a procoagulant environment. The resultant prothrombotic (thrombogenic) surfaces then attract polymorphonuclear cells and platelets, resulting in the endothelium being damaged and causing separation from the underlying substratum, and ultimately, severe thrombosis of the graft. The cell-mediated response is thought to involve not only the T-cell cytotoxicity-effector mechanisms, but also NK and K cell activity.

The standard approach to mitigate the rejection process is to treat the transplant recipient daily with an immunosuppressive regimen. However, currently immunosuppressive regimens are systemic; i.e., in addition to suppressing immune function against the transplanted graft, immune function which protects the recipient from other processes (such as infections) is suppressed. Further, the currently available immunosuppressives may cause substantial non-specific, toxic effects on cell types besides cells comprising the immune system.

For example, a typical immunosuppressive regimen comprises four therapeutic components—steroids, azathioprine, cyclosporin, and anti-T cell antibodies. The use of such therapy may lead to systemic secondary complications. Side effects of long term steroid use include bone disease, cataracts, diabetes, ulcers, pancreatitis and perforation of the colon. The use of azathioprine can cause hematologic toxicity resulting in leukopenia and/or thrombocytopenia; and can cause gastrointestinal complications. Additionally, use of azathioprine results in a significant risk of secondary infection and/or neoplasia. Cyclosporin is nephrotoxic, hepatotoxic, and results in a significant risk for development of hypertension, gingivitis, and neurologic tremors. Administration of anti-T cell antibodies can lead to cytokine-release syndrome, with the most serious complication being acute pulmonary edema. Gastrointestinal complications, typically with severe diarrhea, are common. Central nervous system symptoms may mimic aseptic meningitis, or cause seizures and encephalopathy. In addition to the serious complications with immunosuppressive agents, there is a need to improve efficacy of immunosuppressive therapy. Even in clinical transplantation with the greatly expanded arsenal of immunosuppressive agents, allograft rejection occurs approximately 25% of the time.

In attempting to solve problems associated with xenotransplantation, efforts are directed to mitigating the effect of natural occurring antibodies and the complement cascade. Two research groups (J. P. Richardson of Washington University and J. L. Platt of Duke University in collaboration with Nextran) have focused on temporarily removing the natural occurring antibody by plasmapheresis (or transfecting cells with human genes) with resultant blocking of the complement cascade. Plasmapheresis treatment is only temporary in that the antibody titer quickly returns when the treatments are discontinued. When the natural antibodies return in the circulation, the vascular rejection of the transplanted graft also occurs.

To avoid the systemic complications associated with systemic immunosuppressive therapy, and thereby leave the recipient's immune system intact, the development of a graft-specific therapy which is immunosuppressive or which shields or cloaks the transplanted graft from recipient's immune system is desirable. For example, one approach is to genetically alter a foreign graft (in this case, a xenograft) in the donor before xenotransplantation (*Biomedical Business International Report*, supra). Although several approaches have been taken, the most notable involves the incorporation of membrane associated inhibitors of the complement cascade into graft endothelial cells. There are a number of molecules which have been identified for their ability to inhibit the complement cascade at various points. To name a few, these molecules include: decay accelerating factor, CD46, homologous restriction factor and CDS9. Since these membrane associated inhibitors of complement are species-specific, it is hoped that membrane expression of the molecules in a graft will prevent the transplanted graft from being rejected. However, because the graft rejection process is multifaceted, involving several arms of the immune system, a number of genes would need to be incorporated into graft endothelial cells in order for the transplanted graft to be tolerated by the recipient.

U.S. Pat. No. 5,192,312 (C. Orton) discloses that cells of a graft cannot be masked to reduce immunogenicity. Rather, native cells of the graft must be removed, and replaced with allogeneic or autologous cells in a process involving incubation of the graft with growth factor and allogeneic or autologous fibroblasts prior to transplantation of the graft.

Another approach involves microencapsulated exocrine cells and hepatocytes in attempts to develop a synthetic pancreas and liver, respectively (*Biomedical Business International Report*, supra). Some form of cell attachment substrate is used to enhance function of the islet cells and hepatocytes. However, different substrata matrix lead to different morphology in the cultured cells. Collagen matrix grown hepatocytes had distinct morphology when compared to hepatocytes grown in MATRIGEL™—an extracellular matrix secreted by a Engelberth-Holm-Swarm (EHS) tumor. The matrix components being used as substructure for cell attachment include collagen, fibronectin, laminin, and vitronectin (*Biomedical Business International Report*, supra). MATRIGEL™ is a reconstituted basement membrane from solubilized extract of the basement membrane from the EHS transplantable mouse tumor. Therefore, it is a mouse basement membrane derived from a transformed cell line. In as much, the matrix contains by-products of a transformed cell line such as angiogenic factors. While the EHS tumor-derived extracellular matrix contains laminin, type IV collagen, and heparin sulfate proteoglycans, the ratio of these components are distinct and are not representative of normal basement membranes (Kleinman et al., 1982, *Biochemistry* 22:4969). MATRIGEL™ and type I collagen have been used to support hepatocytes for a synthetic liver.

Thus, there exists a need for expanding the organ donor pool, and a corresponding need for a method to treat a foreign graft in such a way as to be tolerated in a recipient, i.e. thereby avoiding rejection by avoiding activation of a recipient's humoral and cell-mediated immune response to the transplanted graft. The method should also be graft-specific to avoid complications such as those associated with systemic immunosuppressive therapy.

SUMMARY OF THE INVENTION

In accordance with one aspect of the present invention, a method is disclosed to alter the lumenal surface of the vasculature within a graft to be transplanted to render the recipient/donor interface nonimmunogenic and nonthrombogenic, wherein the method disclosed does not incorporate individual proteins, which can be immunogenic of themselves, onto the surface of the vascular endothelial cells. Further, the method involves removing a graft from the donor; preserving the removed graft via an ex vivo process; and then coating the donor's vascular endothelial cells lining the lumen of the blood vessels, within the vascular network of the graft, with a endothelial cell matrix immunologically tolerable (i.e., tolerated as an autograft) to the recipient. Thus, the method of the present invention results in a nonimmunogenic interface between the recipient's immune system and the donor vascular endothelial cells within the transplanted graft. The coated lumenal surface also becomes nonthrombogenic. Additionally, but not necessary to render the transplanted graft as substantially nonimmunogenic and nonthrombogenic, the process provides a surface which, upon transplantation into the recipient, enhances subsequent re-endothelialization of the lumen of the blood vessels of the treated graft with the recipient's own endothelial cells.

In another embodiment of the present invention, rather than allowing for re-endothelialization of the lumen of the blood vessels of the treated graft subsequent to transplantation, an additional step in the ex vivo process is to perfuse the treated graft with vascular endothelial cells immunologically tolerable to the recipient, thereby causing re-endothelialization prior to transplantation into the recipient (adding to the lumenal surface of the vasculature of the treated graft an additional layer which is immunologically tolerable and nonthrombogenic to the recipient).

DETAILED DESCRIPTION OF THE INVENTION

1. Definitions

Figure 1:
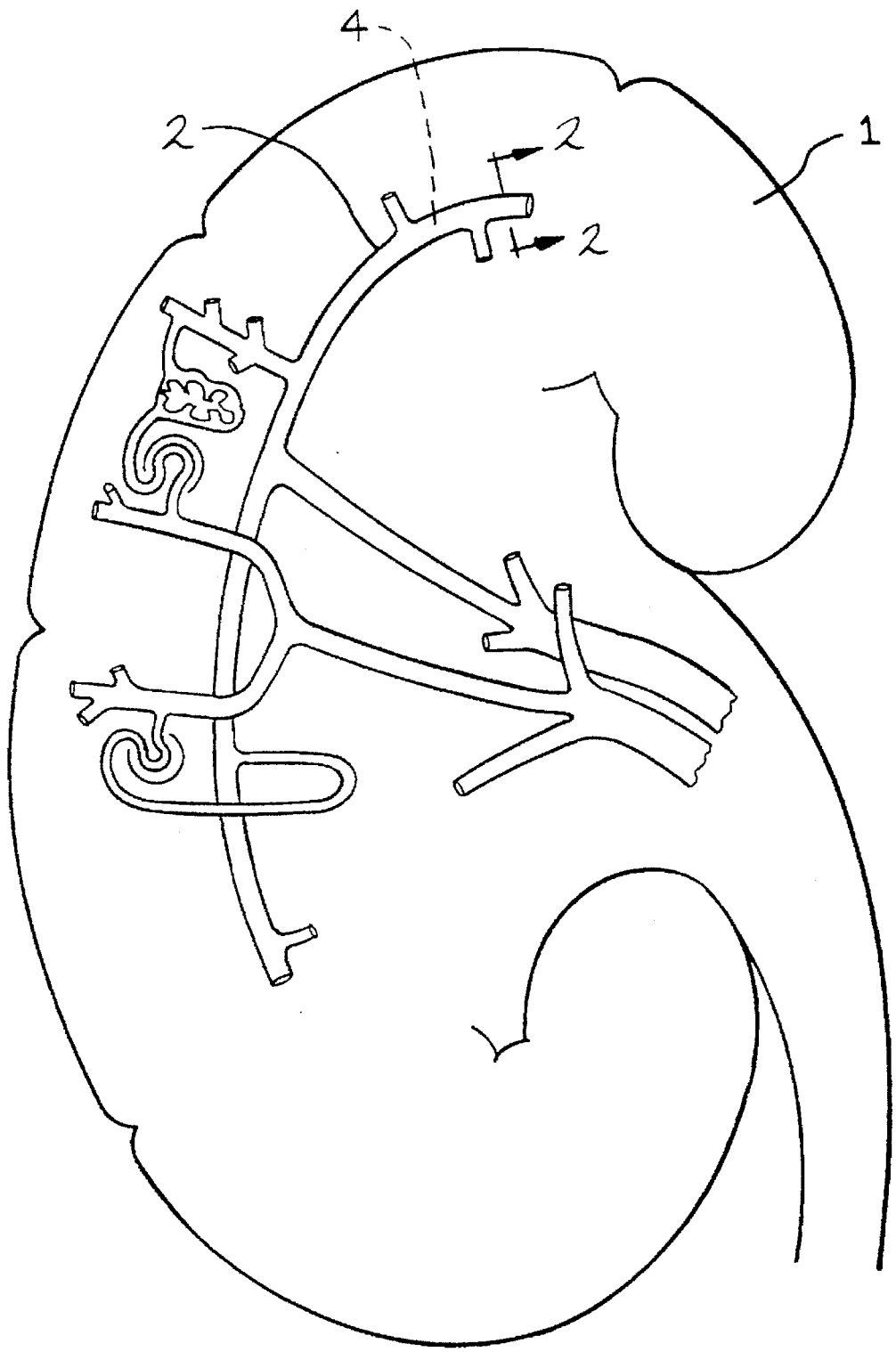
FIG. 1 is a schematic representation of a kidney (1), with blood vessel (2), and lumen (4) thereof.

A "graft" is a term used herein in the specification and claims to mean a transplantable organ or tissue derived from a donor not genetically identical to the recipient. The tissue or organ includes, but is not limited to, skin, kidney, heart, liver, lung, small bowel, pancreas, and eye. Illustrative examples known to those in the art of transplantation include in particular, kiney, liver, aorta and heart. A graft may be an allograft (and thus "allogeneic") which is an organ or tissue from a donor that is the same species as the recipient. Alternatively, the graft may a xenograft (and thus "xenogeneic") which is an organ or tissue from a donor that is a species other than the species of the recipient.

"Foreign" is a term used herein in the specification and claims to mean antigens on a graft recognized as other than self (recipient) antigens.

"Immunologically tolerable" are terms used herein in the specification and claims to mean a graft tolerated as an allograft or autograft. In degree of immune recognition directed to a graft, and severity of a subsequent rejection process of a graft, an autograft is minimal, if any; and an allograft is less severe than a xenograft. For example, the rejection process of an allograft make take several days to develop; whereas the process for a xenograft is so ferocious, that the onset of the rejection process occurs within hours, or even in minutes.

"Interface" or "recipient/donor interface" are terms used herein in the specification and claims to mean a point at which the recipient's immune system reacts with donor graft cells to initiate the rejection process. More particularly, the interface is at the donor's vascular endothelial cells comprising the lumenal surfaces of the vasculature of a graft since: (a) graft damage and the humoral rejection process appear to begin when the recipient's antibodies bind to foreign antigens on the surface of the donor's vascular endothelial cells comprising the lumenal surfaces of the vasculature of a graft; and (b) subsequent damage of and destruction of a graft by humoral or cell-mediated mechanisms are directed to a principal target, the donor's vascular endothelial cells which line the blood vessels of the graft.

"Nonthrombogenic" is a term used herein in the specification and claims to mean a property of preventing blood coagulation, and as characteristic of normal, healthy, undamaged cells. "Substantially nonimmunogenic" is a term used herein in the specification and claims to mean a property of preventing an immune response. For purposes of illustration, using the method of the present invention for rendering a graft substantially nonimmunogenic by treating the graft with extracellular matrix, the extracellular matrix provides greater than approximately 99% inhibition in cell-mediated reaction to the treated graft as compared to that against an untreated graft. "Immunomodifying" or "immunomodification" is a term used herein in the specification and claims to mean a process of rendering a graft substantially nonimmunogenic and nonthrombogenic.

"Extracellular matrix" is a term used herein in the specification and claims to mean isolated basement membrane produced by vascular endothelial cells and a membrane on which the cells rest in vivo. Generally, extracellular matrix comprises proteins such as type IV and V collagens, vitrogen, fibronectin, laminin, entactin, and nidogen; and glycosaminoglycans and proteoglycans. However, it is noted that the extracellular matrix can vary in molecular size, composition, and structural assembly, depending on its anatomic origin. Despite the variation due to anatomic origin, extracellular matrix from any anatomic site is useful in the present invention. That is, whether produced and isolated from corneal vascular endothelial cells or liver vascular endothelial cells, extracellular matrix can provide a substantially nonimmunogenic and nonthrombogenic surface for grafts using the method of the present invention. However, the choice of using an extracellular matrix derived from the anatomic source of the same type as the graft to treat the graft according to the method of the present invention may be helpful in optimizing recolonization posttransplant, or seeding pretransplant, in a treated graft.

2. General considerations

While it is known to those skilled in the art that extracellular matrix can be used as a matrix upon which to grow cells in culture, it has not been described that endothelial cells could be maintained (survive and function) underneath a coating of extracellular matrix for extended periods of time. In particular, at the time of the invention it was not known whether a coating of extracellular matrix over vascular endothelial cells (such as those of a graft) would (a) allow for transport of nutrients and oxygen from the blood stream to the vascular endothelial cells located beneath the extracellular matrix coating; (b) render such vascular endothelial cells substantially nonimmunogenic; (c) render such vascular endothelial cells nonthrombogenic; (d) simultaneously support recolonization by recipient vascular endothelial cells while supporting the maintenance of coated donor vascular endothelial cells; nor disclosed was a method for coating the recipient/donor interface of a graft with extracellular matrix to render the interface and graft substantially nonimmunogenic and nonthrombogenic. Further, unlike the method disclosed in U.S. Pat. No. 5,192,312, in the method according to the present invention the donor graft cells do not need to be removed, thereby reducing any risk of damage to the graft from such manipulations.

It appears that extracellular matrix generally does not vary in antigenicity from individual to individual of a given species, i.e. only in a few cases out of thousands of transplants has anti-basement membrane antibodies been detected in transplant patients. Thus, it appears that allotypes for extracellular matrix are exceedingly rare. In the present invention, disclosed is a method which comprises removing the graft to be transplanted from a donor, and preserving the removed graft so that it can be immunomodified by a coating with extracellular matrix. The preservation of the graft for immunomodification can include any preservation process known to those skilled in the art, and includes a process known to the present inventor for maintaining ongoing metabolism by pumping the graft with a perfusate composed of a highly enriched tissue culture medium which is supplemented with an oxygen carrier such as a perfluorochemical emulsion (U.S. patent application Ser. No. 08/033,629 disclosing "warm preservation technology"). Grafts being preserved ex vivo are then immunomodified by coating the vascular endothelial cell lining the lumen (also termed herein as the "lumenal surface") of the blood vessels within the vascular network of the graft. The material used to coat the lumenal surface comprises an extra-cellular matrix which promotes vascular endothelial cell attachment and proliferation. The method according to the present invention results in a nonimmunogenic interface between recipient/donor. The lumenal surface is also rendered nonthrombogenic by the coating with extracellular matrix coating. An advantage of the method according to the present invention is that the extracellular matrix coating provides a surface which enhances the re-endothelialization of a treated graft with the recipient's endothelial cells subsequent to transplantation. Alternatively, autologous or allogeneic vascular endothelial cells, which are introduced subsequent to coating with the extracellular matrix but before transplantation into the recipient, may be used to "seed" the treated graft; i.e., in colonizing the treated graft before transplantation. The extracellular matrix coating supports such colonization of vascular endothelial cells by promoting adhesion, regulating growth factor activity, modulating protease activity, and by directly activating intracellular second messenger systems.

EXAMPLE 1

Isolation of Extracellular Matrix

Extracellular matrix may be produced as a membrane in vitro from cultured vascular endothelial cells. The isolation process involves removing the endothelial cells by a nonenzymatic process such as use of a buffered detergent solution. The extracellular matrix produced in vitro is solubilized by acidification in the cold by adding a weak acid solution (such as 0.1N HCl) to the membrane surface and incubating the mixture for thirty minutes at 4° C. The solubilized membrane can then be stored frozen until use. Upon thawing, the membrane is brought to a neutral pH by using an alkaline solution (such as 0.1N NaOH) before use as a coating of the lumenal surfaces of the blood vessels within the vascular network of the graft. The membrane, adjusted to a neutral pH, will polymerize at a temperature range of 25° C. to 37° C. at a temperature-related rate.

EXAMPLE 2

Choice of Coating Material—Extracellular Matrix

In vivo, cells rest on extracellular matrix. It is the natural substrate on which cells migrate, proliferate, and differentiate. The endothelial cells' extracellular matrix is composed of varying amounts of different collagens, glycosaminoglycans, proteoglycans, and glycoproteins—most notably fibronectin. These components are linked in such a way that the resulting structure is a tri-dimensional scaffolding in vivo. Thus, the extracellular matrix provides scaffolding, support and strength to cells grown on it, allowing those cells to differentiate and mediate physiologic responses.

Extracellular matrices from different anatomic sites may vary in their ability to support and allow for proper differentiation of cells not from that respective anatomic site. Although, extracellular matrix derived from any anatomic site would promote efficient attachment of recipient's or allogeneic vascular endothelial cells, extracellular matrix derived from the respective anatomic site of the graft would likely provide optimal conditions for cell proliferation of colonizing vascular endothelial cells. Further, although it appears not to be required, the extracellular matrix should be produced from cells derived from the same species as the recipient. Thus, if the recipient is a human, a preferred extracellular matrix is a matrix made from human vascular endothelial cells since it is the most natural surface for such endothelial cells; and provides matrix recognition domains and corresponding cell receptors specific for, and enhancing the growth of, human vascular endothelial cells which colonize the graft subsequent to coating. As stated above, it is not a requirement that the extracellular matrix used for coating be produced from vascular endothelial cells of the same anatomic origin as the graft to be treated. For example, an extracellular matrix that appears to provide surfaces, of grafts of different anatomical origin, coated with it to become efficiently seeded/colonized with vascular endothelial cells, is corneal endothelial extracellular matrix.

EXAMPLE 3

The Coating Process

The method of the present invention for immunomodifying a graft involves a process of coating the lumenal surfaces of the vasculature of the graft with an extracellular matrix preferably produced from vascular endothelial cells derived from the same species as the recipient; thereby providing coated lumenal surfaces which are not recognized as foreign when the graft is transplanted into a recipient. Further, the extracellular matrix coating provides a surface for re-endothelialization by the recipient's vascular endothelial cells posttransplantation, or by autologous or allogeneic vascular endothelial cells seeded onto the treated graft prior to transplantation. In either case, the vascular endothelial cells which grow onto the extracellular matrix coating of a treated graft provide an additional interface between the donor graft vascular endothelial cells and the recipient's immune surveillance mechanisms, for the purpose of preventing or minimizing the recognition of the graft as foreign and subsequent graft rejection.

Figure 2:
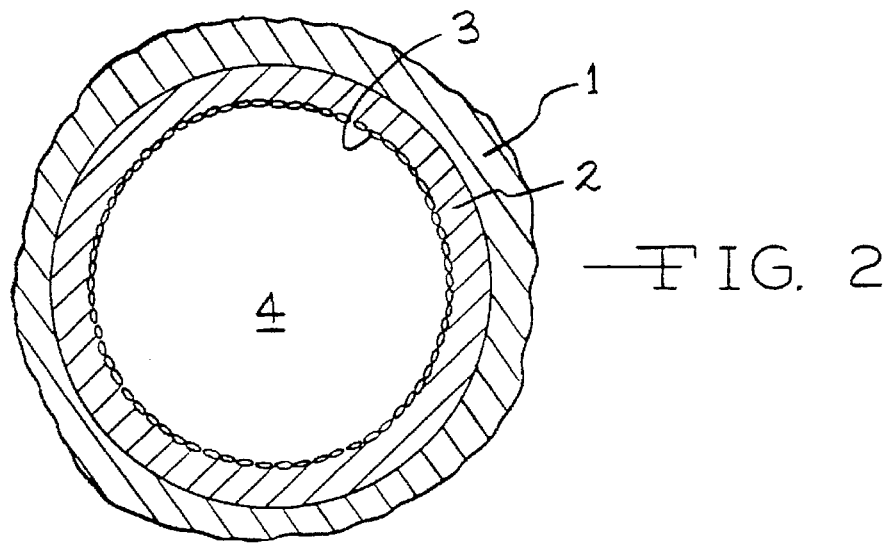
FIG. 2 shows a cross-sectional view of blood vessel (2), vascular endothelial cells (3) lining blood vessel (2), and blood vessel lumen (4).
Figure 3:
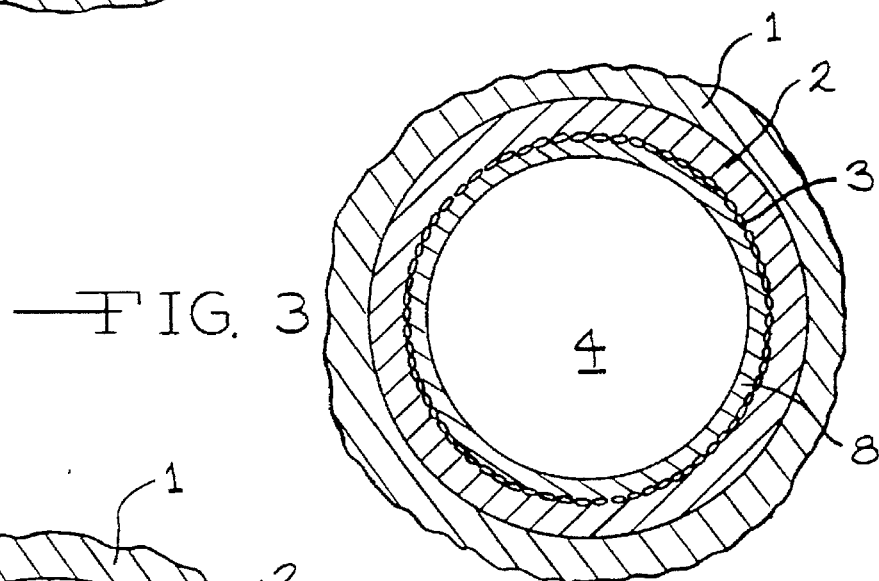
FIG. 3 represents coating with extracellular matrix (8) over vascular endothelial cells (3) lining blood vessel (2), as shown in this cross-sectional view.
Figure 4:
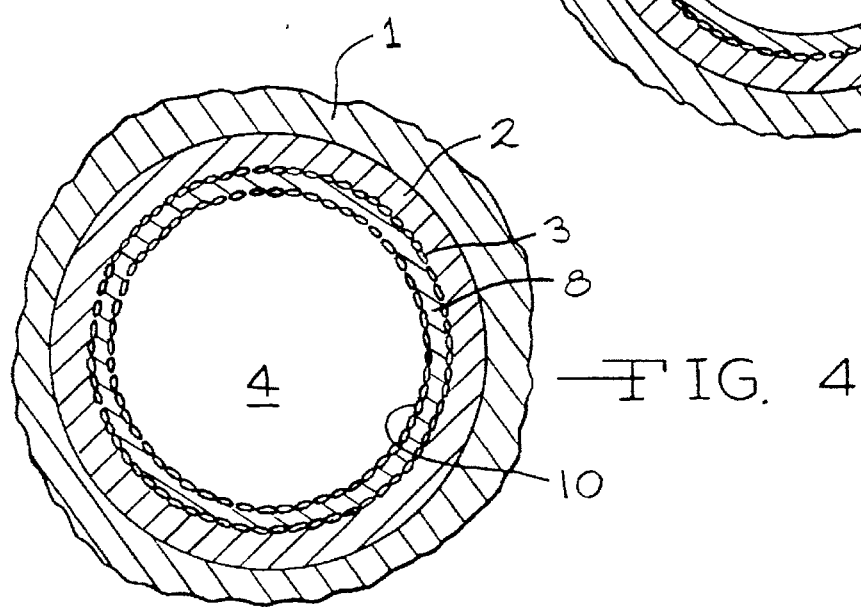
FIG. 4 represents re-endothelialization with recipient or allogenic vascular endothelial cells (10) of the matrix (8) which coats vascular endothelial cells (3) of blood vessel (2), as shown in this cross-sectional view.

Extracellular matrix (also known as basement membrane) has been used as a surface on which to grow cells. However in contrast, in the method of the present invention, the extracellular matrix is used as a coating or "sandwich" utilized to hide underneath it the donor vasculature endothelial cells from the recipient's immune surveillance mechanisms. Further, such coating provides a surface exposed to the lumen onto which recipient vascular endothelial cells can attach and proliferate (re-endothelialization); i.e., an additional means for preventing graft recognition as foreign and subsequent rejection. The laminin and fibronectin portions of the extracellular matrix bind to the surface of the endothelial cells in vivo. Schematic representations of the method of the present invention for immunomodifying a graft are shown in FIGS. 1–4, wherein the graft, used for illustration purposes, consists of a kidney (1), showing a cross-section of kidney blood vessel (2). The vascular endothelial cells(3) of blood vessel (2) are fully coated with extracellular matrix (8), wherein matrix (8) then serves as a surface for re-endothelialization by a recipient's, or allogeneic, vascular endothelial cells (10). Thus, for the coating process to be effective, it must render the coated lumenal surfaces of the vasculature of the graft as:

1. nonimmunogenic (with respect to the recipient);
2. nonthrombogenic (i.e. maintaining the viability and normal homeostasis in the coated donor endothelial cells); and
3. supportive of, and efficiently promoting re-endothelialization.

According to the method of the present invention, a graft to be transplanted is first removed from the donor and placed in a preservation solution (ex vivo). The preservation solution is a physiologically compatible solution to the graft, thereby maintaining graft cell viability and integrity. Essentially, the preservation solution may comprise a buffered salt solution supplemented with protein and/or other components helpful in maintaining cell viability or integrity. A basal cell culture medium could also be used as a preservation solution (known in the art such as M199, DMEM, etc.). Such cell culture medium may also be supplemented, such as with serum albumin. Other examples of a preservation solution include a phosphate buffer with serum protein supplementation or containing a serum substitute.

If a warm preservation technique is to be used in the ex vivo process, a preferred preservation solution is recited in Table 1.

TABLE 1

| | |
|---|---|
| DL-Alanine | .12 g/L |
| L-Arginine HCl | .14 g/L |
| DL-Aspartic Acid | .12 g/L |
| L-Cysteine HCL•H$_2$O | .00022 g/L |
| L-Cystine 2HCl | .052 g/L |
| DL-Glutamic Acid | .2672 g/L |
| L-Glutamine | .2 g/L |
| Glycine | .1 g/L |
| L-Histidine HCl•H$_2$O | .04376 g/L |
| L-Hydroxyproline | .02 g/L |
| DL-Isoleucine | .08 g/L |
| DL-Leucine | .24 g/L |
| L-Lysine HCl | .14 g/L |

TABLE 1-continued

| | |
|---|---|
| DL-Methionine | .06 g/L |
| DL-Phenylalanine | .10 g/L |
| L-Proline | .08 g/L |
| DL-Serine | .10 g/L |
| DL-Threonine | .12 g/L |
| DL-Tryptophan | .04 g/L |
| L-Tyrosine•2Na | .11532 g/L |
| DL-Valine | .10 g/L |
| Adenine Hemisulfate | .02 g/L |
| Adenosine Triphosphate•2Na | .002 g/L |
| Adenylic Acid | .0004 g/L |
| Alpha Tocopherol Phosphate•2Na | .00002 g/L |
| Ascorbic Acid | .0001 g/L |
| D-Biotin | .00002 g/L |
| Calciferol | .0002 g/L |
| Cholesterol | .0024 g/L |
| Choline Chloride | .001 g/L |
| Deoxyribose | .001 g/L |
| Folic Acid | .00002 g/L |
| Glutathione (Reduced) | .0001 g/L |
| Guanine HCl | .0006 g/L |
| Hypoxanthine | .0006 g/L |
| Menadione (Na Bisulfite) | .00003 g/L |
| Myo-Inositol | .0001 g/L |
| Niacinamide | .00005 g/L |
| Nicotinic Acid | .00005 g/L |
| PABA | .0001 g/L |
| D-Pantothenic Acid Ca | .00002 g/L |
| Polyoxyethylenesorbitan Monooleate | .04 g/L |
| Pyridoxal HCl | .00005 g/L |
| Pyridoxine HCl | .00005 g/L |
| Retinol Acetate | .00028 g/L |
| Riboflavin | .00002 g/L |
| Ribose | .001 g/L |
| Thiamine HCl | .00002 g/L |
| Thymine | .0006 g/L |
| Uracil | .0006 g/L |
| Xanthine•Na | .00069 g/L |
| Calcium chloride•2H$_2$O | .265 g/L |
| Ferric Nitrate•9H$_2$O | .00144 g/L |
| Magnesium sulfate (anhydrous) | 1.204 g/L |
| Potassium chloride | .4 g/L |
| Sodium Acetate (anhydrous) | .1 g/L |
| Sodium Chloride | 6.8 g/L |
| Sodium Phosphate Monobasic (anhydrous) | .244 g/L |
| Glucose | 2.0 g/L |
| Insulin | .01 g/L |
| Bovine serum albumin (BSA) | 30.0 g/L |
| NaHCO$_3$ | 4.4 g/L |
| Pyruvate | .22 g/L |
| Transferrin | 1 g/L |
| serum | 100 ml |
| Impermeant (Cyclodextrin) | .5 g/L |
| Mucopolysaccharide (chondroitin sulfate B) | .004 g/L |
| ENDO GRO™ (growth factor) | .20 g/L |
| heparin | .18 g/L |
| perfluorochemical emulsion* | 20% (v/v) |

*-perflubron emulsion as an oxygen carrier

In this ex vivo process, the graft may be maintained with circulation of the preservation solution as a perfusate at a flow rate appropriate for the vascular flow of the graft (ex. for a kidney, 100 cc–200 cc per minute). The extracellular matrix can then be added (amount depending on the lumenal surface area of the graft) to the perfusate via the warm preservation process to coat the lumenal surface of the vasculature within the graft. The extracellular coating can polymerize as a gel comprising a thin continuous sheet along the lumenal surface of the blood vessels within the graft. The polymerization occurs at a temperature-related rate (above 22° C.); i.e., more quickly as the temperature is raised and its binding is receptor driven. The polymerizing extracellular matrix membrane attaches to the surface of the donor's vascular endothelial cells via a specific cell surface receptor such as the RGD sequences.

The minimal amount of extracellular matrix to be added is calculated by estimating the lumenal surface area of the vasculature within the graft. In general, a range of 5.2 mg to 26 mg (wet weight) of extracellular matrix per cm$^2$ of lumenal surface area may be used in the perfusate to coat the lumenal surfaces of a graft. However, a greater concentration of extracellular matrix may be used to ensure complete coating of the lumenal surfaces of the vasculature within the graft during the ex vivo process. After an incubation of approximately 60 minutes at 25° C., or approximately 30 minutes at 37° C., for complete polymerization, the treated graft is then available for transplantation into the recipient.

Alternatively, in a ex vivo process of applying the membrane without a warm preservation technique, a preservation solution containing partially polymerized extracellular matrix (amount depending on the lumenal surface area of the graft) is infused into the vasculature of the graft just prior to reimplantation. The final polymerization occurs during the period of reimplantation, while the vessels are reanastamosed.

EXAMPLE 4

Maintenance of Coated Vascular Endothelial Cells

When vascular endothelial cells have been coated with extracellular matrix according to the method of the present invention, the cells maintained underneath the coating remain viable. For example, in vitro studies involving human umbilical vein endothelial cells have been used to determine the viability of cells kept under the extracellular matrix in tissue culture, as opposed to traditional approaches of using the matrix below cells in culture. This was done by overlaying a culture of human umbilical vein endothelial cells with enough endothelial cell-derived extracellular matrix to fully cover (coat) the cultured cells. The endothelial cells, in each well of a 96 well culture plate, were coated with approximately 26 mg of matrix per mm$^2$ of surface area. Endothelial cells can be maintained underneath this extracellular matrix for extended periods of time (at least 7 days). The vascular endothelial cells coated by extracellular matrix do not proliferate and migrate through the extracellular matrix, nor is there any interruption detected in the membrane. Similar results were obtained when lengths of human umbilical cords (ranging from about 12 inches to about 24 inches) were treated according to the method of the present invention. Histological evaluation of cross-sections of the treated umbilical cord, after maintenance under the coating for seven days post-treatment, revealed normal vasculature architecture of the cells and tissue contained below the extracellular coating. Thus, while the membrane or coating of extracellular matrix serves to cloak the donor graft vascular endothelial cells from the recipient's immune effector mechanisms (humoral and cell-mediated immune responses), thereby rendering the graft substantially nonimmunogenic and nonthrombogenic, the extracellular matrix also allows for the free transport of nutrients and oxygen for the maintenance of cells below the coating.

Upon subsequent enzymatic passage in tissue culture which also causes the disruption of the extracellular matrix coating of vascular endothelial cells treated as described, such cells have demonstrated normal characteristics of vascular endothelial cells in tissue culture; i.e. the ability to attach, proliferate, and express normal phenotypes (such as Factor VIII antigen), morphology and function.

EXAMPLE 5

Nonimmunogenicity of Coated Graft

To illustrate that a coated graft could be rendered nonimmunogenic using the method of the present invention, an extreme challenge model was used; namely a xenograft model. The mixed lymphocyte culture assay is a test system used by those skilled in the art of organ transplantation to predict the fate of a graft if transplanted. A mixed lymphocyte-endothelial cell reaction was used to evaluate the immunologic status of a coated xenograft endothelium. The mixed lymphocyte-xenograft endothelial cell reaction represents a minigraft situation wherein the immunoproliferative response can be measured.

In accordance with the methods of Examples 2 & 3, in this model, for purposes of illustration, the xenograft comprised confluent human vascular endothelial cells which were treated using the process of the present invention with extracellular matrix. The extracellular matrix used for coating in this illustration was bovine-derived (commercially available as ENDOMATRIX™, VEC TEC Inc.). As controls, also tested separately by the mixed lymphocyte-endothelial cell reaction were a) uncoated human endothelial cells, and b) the bovine-derived extracellular matrix. Bovine mononuclear cells ($1\times10^4$ cells/well, 96 well plate) were added to each of the coated culture and control cultures and incubated at 37° C. for 5 days. An additional control was a culture of the bovine mononuclear cells ("responding lymphocytes") themselves. On day 5 the cultures were pulsed with 0.6 uCi of $^3$H-thymidine and harvested 18 hours later. The incorporation of any radiolabel into the cultures was evaluated using a scintillation counter. Since the radioactive thymidine is incorporated into the DNA of cells during cell proliferation, incorporation of significant amounts of the radiolabel would occur only in the recognition by the bovine lymphocytes of the human vascular endothelial cells as being foreign. Thus, the recipient lymphocytes are mixed with donor cells, and if the recipient lymphocytes recognize the donor cells as foreign tissue, the lymphocytes then respond by proliferating thereby causing $^3$H-thymidine incorporation. The endothelial cells cannot proliferate in this system because they are used in a confluent state, whereby endothelial cell growth is contact-inhibited. The results of the mixed lymphocyte-xenograft endothelial cell reaction are displayed in Table 2 below. It can be seen from the results in Table 2, that coating vascular endothelial cells with endothelial extracellular matrix alone provides greater than 99.9% inhibition of the responding lymphocytes in the cell proliferative response to the xenograft (i.e. primary sensitization). Thus, coating vascular endothelial cells with the extracellular matrix according to the method of the present invention blocks the recognition of the xenograft endothelium by the bovine recipient lymphocytes and renders the graft substantially nonimmunogenic.

The calculated stimulation indices of the control response in the three experiments were: 36.1, 79.4, and 20.29. In this type of assay, a stimulation greater than 5.0 is considered positive and represents incompatibility whereby the recipient recognizes the donor tissue as foreign. Using the method according to the present invention, this immune response against the donor graft was effectively prevented, as indicated by the stimulation indices of 0.7, 1.0, and 1.21.

TABLE 2

| Experiment | CPM* | SI* | % Inhibition* |
|---|---|---|---|
| 1 | | | |
| Responding lymphocytes alone | 376 | — | |
| Responding lymphocytes & vascular endothelial cells | 13,581 | 36.1 | |

TABLE 2-continued

| Experiment | CPM* | SI* | % Inhibition* |
|---|---|---|---|
| Responding lymphocytes & matrix coated vascular endothelial cells | 248 | 0.7 | 99.98% |
| Responding lymphocytes & matrix alone | 368 | 1.0 | |
| 2 | | | |
| Responding lymphocytes | 192 | — | |
| Responding lymphocytes & vascular endothelial cells | 15,251 | 79.4 | |
| Responding lymphocytes & matrix coated vascular endothelial cells | 189 | 1.0 | 99.99% |
| Responding lymphocytes & matrix alone | 299 | 1.6 | |
| 3 | | | |
| Responding lymphocytes | 278 | — | |
| Responding lymphocytes & vascular endothelial cells | 5,640 | 20.29 | |
| Responding lymphocytes & matrix coated vascular endothelial cells | 337 | 1.21 | 99.94% |
| Responding lymphocytes & matrix alone | 273 | 1.0 | |

*Mean of triplicate cultures
CPM - counts per minute
SI - Stimulation Index
% Inhibition - of xenograft response inhibited by coating with the extracellular matrix.

EXAMPLE 6

Coated Vascular Endothelial Cells are Rendered Nonthrombogenic

In vivo platelet aggregation does not occur with exposure to intact basement membrane found immediately subendothelium. Thus, the type IV and V collagens found in extracellular matrix do not elicit platelet responses such as aggregation. It has also been observed that platelets and neutrophils appear not to stick to extracellular matrix. To illustrate that extracellular matrix can provide a nonthrombogenic surface, cells treated according to the method of the present invention were analyzed for their thrombotic activity.

Using the methods of the present invention according to Examples 2 & 3, cultures of confluent human vascular endothelial cells, either untreated or coated with extracellular matrix were evaluated, after being in a confluent state for 24 hours, for surface resistance to thrombogenesis. In this assay, if the coating process damages the endothelial cell surface, or if the coating material itself is thrombogenic, the surface then becomes thrombogenic (i.e. increased ability to bind platelets). Platelets labelled with ethidium bromide were added to the two groups of cultures. After 30 minutes the cultures were washed to remove nonadhered platelets. The degree of platelet adherence was evaluated microscopically in the two groups. There was no statistical difference in platelet binding rates between untreated vascular endothelial cells, and vascular endothelial cells coated with extracellular matrix in accordance with the method of the present invention. These studies confirm reports where basement membrane was exposed to the bloodstream, platelets did not aggregate. This phenomenon is markedly different from the prothrombogenic process of platelets aggregating when in contact with interstitial collagen (collagen types I, II, and III).

EXAMPLE 7

Re-endothelialization of Coated Vascular Endothelial Cells

A further embodiment of the present invention is that subsequent to extracellular matrix coating of graft vascular endothelial cells, the extracellular matrix coating may then be used as a surface for re-endothelialization either by the recipient's vascular endothelial cells posttransplantation, or by autologous or allogeneic vascular endothelial cells seeded onto the treated graft prior to transplantation. Although extra-cellular matrix is a natural substrata for vascular endothelial cells, it was not known whether an extracellular matrix could serve as both a coating laid over vascular endothelial cells, and a substrata that supports recolonization by vascular endothelial cells and further supports their growth and maintenance. Using the methods of the present invention according to Examples 2 & 3, an in vitro assay was performed to illustrate the ability of the extracellular matrix to serve as both a coating and a substrata for vascular endothelial cells. Human umbilical vein endothelial cells, adjusted to a concentration of approximately $2.5 \times 10^5$ cells/ml, were added to culture surfaces of 25 cm$^2$. In one instance, the culture dish surface was coated with extra-cellular matrix by overlaying the matrix onto the surface before seeding it with vascular endothelial cells. As a control, the vascular endothelial cell culture surface remained untreated. At various time points after seeding the culture surfaces with vascular endothelial cells, the unattached cells of the control and coated test culture surfaces were washed away. The cultures were evaluated microscopically each day and fed every other day until confluent. As shown in Table 3, the extracellular matrix coating promoted the attachment and growth of newly seeded endothelial cells and stabilized the morphogenesis.

TABLE 3

| | Seeding Studies | | | |
| --- | --- | --- | --- | --- |
| | Time | | | |
| | 15 mins. | 30 mins. | 24 hours | confluence |
| nontreated surface | 0 | <1 | 1 | 10 days |
| matrix-coated surface | +1 | +2 | +3 | 4 days | scoring:

0 - no attached cells visible
1 - + 1 - sparse attachment
2 - + 2 - 50% coverage of surface
3 - + 3 - 80% coverage of surface
confluence-total coverage of surface with tight junction As can be seen from the results of this assay, extracellular matrix can simultaneously serve as a coating and a substrata for vascular endothelial cells. Thus, one embodiment of the present invention involves natural colonization of a treated graft posttransplant with the recipient's own vascular endothelial cells. Such vascular endothelial cells which recolonize onto the extracellular matrix coating of a treated graft can proliferate and thus provide an additional interface between the donor graft vascular endothelial cells and the recipient's immune surveillance mechanisms, for the purpose of preventing or minimizing the recognition of the graft as foreign and subsequent graft rejection.

EXAMPLE 8

The in vitro models and methods illustrated in Examples 2–7 show that using the method according to the present invention, a graft may be immunomodified by coating the lumenal surface (vascular endothelial cells) of the vasculature within the graft to interrupt the recipient and donor interface with an extracellular matrix which will render the graft so treated: 1) nonimmunogenic by masking the graft antigen surface comprising the donor's vascular endothelial cells; 2) nonthrombogenic; and 3) if desired, supportive of efficient reseeding of the surface of the extracellular matrix, exposed to the lumenal opening, with recipient or allogeneic vascular endothelial cells.

To illustrate the method of the present invention in immunomodifying a graft ex vivo, comprising a kidney intended for transplantation in a recipient, the graft is removed from the donor. Using the preservation solution and the methods according to Example 1, the graft comprising the kidney is flushed with the solution (recited in Table 1) upon retrieval. At temperatures in the range of about 22° C. to 35° C., the graft may be stored using a preservation system in the preservation solution for time periods of up to at least 18 hours as long as the metabolism is supported, i.e., the pH is monitored and regulated such as by appropriately adjusting the flow of $O_2$ and $CO_2$, the rate of diuresis, and glucose utilization. During the storage period, the graft is maintained as described above with circulation of the preservation solution as a perfusate at a flow rate appropriate for the vascular flow of the graft (for the kidney, 100 cc–200 cc per minute through the perfusion period). Circulation through the graft via a warm preservation system enables the removal of toxic metabolic wastes. During the ex vivo perfusion period, and prior to transplantation, the extracellular matrix can be added to the perfusate to coat the lumenal surface of the vasculature within the graft. The minimal amount of extracellular matrix to be added is calculated by estimating the lumenal surface area of the vasculature within the graft. For example, for a human kidney or porcine kidney, a range of 5.2 mg to 26 mg (wet weight) of extracellular matrix per cm$^2$ of lumenal surface area may be used in the perfusate. Thus, for a kidney graft weighing approximately 35 grams, the concentration of the extracellular matrix in the perfusate may be in the range of 50 to 100 cc of wet matrix preparation. However, a greater concentration of extracellular matrix may be used to ensure complete coating of the lumenal surfaces of the vasculature within the graft during the perfusion period.

TABLE 4

| Metabolic Function During Graft Perfusion/Coating | | |
| --- | --- | --- |
| | At 25° C. | At 32° C. |
| $O_2$-consumption + | 4.8 ml/min | 5.7 ml/min |
| diuresis | 143.1 cc/hr | 123.3 cc/hr |
| histology | normal | normal |
| glucose utilization | 93 mg/dl | 165 mg/dl |

* specimens collected after 6 hours of renal perfusion and represents the mean from experimental data in each group
+ calculated using the method of Fick Alternatively, the kidney graft can be immunomodified by a process without warm preservation. The extracellular matrix in a preservation solution (in a range of 5.2 mg to 26 mg wet weight of extracellular matrix per cm$^2$ of lumenal surface area) can be neutralized and partially polymerized by warming it to 37° C. for approximately 20 minutes. The partially polymerized matrix can then be infused into the kidney graft prior to transplantation, during which time the infused matrix can fully polymerize.

EXAMPLE 9

In accordance with the methods of the present invention, and as illustrated by Example 8, a graft such as a kidney may be immunomodified ex vivo, and prior to transplantation into a recipient, by coating the lumenal surfaces of the vasculature within the graft. Although as demonstrated in Examples 2–6, coating donor vascular endothelial cells with extracellular matrix provides a donor/recipient interface that is nonimmunogenic, nonthrombogenic and supportive of re-endothelialization by the recipient's vascular endothelial cells, in another embodiment of the present invention it may be desirable to facilitate re-endothelialization prior to transplantation in the recipient. This can be accomplished by adding vascular endothelial cells, allogenic or preferably autologous with respect to the recipient, to the preservation solution for perfusion or infusion subsequent to the coating process.

Such vascular endothelial cells can be isolated from tissue by collecting the tissue aseptically and storing it at 4° C. in media containing antibiotics. The tissues were minced and incubated in a 0.2% collagenase solution for digestion. The digested material was passed through nylon mesh screens to remove the large tissue fragments. The filtrate was then layered onto a 45% percoll gradient and centrifuged at 10,000×g for 20 minutes. The layer of vascular endothelial cell tufts were collected and washed. The vascular endothelial cells were diluted by limited dilution for cloning inoculation into 96 well tissue culture plates. After incubation in culture at 37° C., the cells were evaluated for expression of Factor VIII. Monolayers of fibroblasts served as negative controls in the Factor VIII antigen expression, whereas umbilical vein endothelial cells served as the positive controls. Those cells expressing Factor VIII antigen and morphologically exhibiting properties of endothelial cells were pooled and mass cultured for each of the different anatomic sites by seeding 25 cm$^2$ flasks at a cell concentration of $5 \times 10^3$/cm.

Alternative sources may be vascular endothelial cells isolated from cell culture (ex. culture of recipient's own cells) or vascular endothelial cells isolated from umbilical cords. Thus, if a graft is to be coated with human vascular endothelial cells, a convenient source of such cells are human umbilical cords which contain long lengths of unbranched blood vessels comprised of two arteries and one vein.

EXAMPLE 10

Using the methods outlined according to Examples 2, 3, and 8, a graft comprising a mammalian heart is immunomodified by coating the lumenal surfaces in the vasculature within the graft with extracellular matrix in the ex vivo perfusion or infusion process.

EXAMPLE 11

Using the methods outlined according to Examples 2, 3, 8, and 9, a graft comprising a mammalian heart is immunomodified by coating the lumenal surfaces in the vasculature within the graft with extracellular matrix in the ex vivo perfusion or infusion process. In addition, re-endothelialization of the graft is facilitated by adding vascular endothelial cells derived from the same species as the recipient (allogeneic or preferably autologous) subsequent to the coating process by perfusion or infusion, but before transplantation into the recipient; or alternatively, by natural re-endothelialization with recipient's own endothelial cells posttransplantation.

EXAMPLE 12

Using the methods outlined according to Examples 2, 3, and 8, a graft comprising a mammalian lung is immunomodified by coating the lumenal surfaces in the vasculature within the graft with extracellular matrix in the ex vivo perfusion or infusion process.

EXAMPLE 13

Using the methods outlined according to Examples 2, 3, 8, and 9, a graft comprising a mammalian lung is immunomodified by coating the lumenal surfaces in the vasculature within the graft with extracellular matrix in the ex vivo perfusion or infusion process. In addition, re-endothelialization of the graft is facilitated by adding vascular endothelial cells derived from the same species as the recipient (allogeneic or preferably autologous) subsequent to the coating process by perfusion or infusion, but before transplantation into the recipient; or alternatively by natural re-endothelialization with recipient's own endothelial cells posttransplantation.

EXAMPLE 14

Using the methods outlined according to Examples 2, 3, and 8, a graft comprising a mammalian liver is immunomodified by coating the lumenal surfaces in the vasculature within the graft with extracellular matrix in the ex vivo perfusion or infusion process.

EXAMPLE 15

Using the methods outlined according to Examples 2, 3, 8, and 9, a graft comprising a mammalian liver is immunomodified by coating the lumenal surfaces in the vasculature within the graft with extracellular matrix in the ex vivo perfusion or infusion process. In addition, re-endothelialization of the graft is facilitated by adding vascular endothelial cells derived from the same species as the recipient (allogeneic or preferably autologous) subsequent to the coating process by perfusion or infusion, but before transplantation into the recipient; or alternatively by natural re-endothelialization with recipient's own endothelial cells posttransplantation.

EXAMPLE 16

As disclosed herein, for the method of immunomodifying a graft to be effective, the coating process must render the coated lumenal surfaces of the vasculature of the graft as:

1. nonimmunogenic (with respect to the recipient);
2. nonthrombogenic (i.e. maintaining the viability and normal homeostasis in the coated donor vascular endothelial cells); and
3. supportive of, and efficiently promoting re-endothelialization.

Extracellular matrix is composed of varying amounts of different collagens, glycosaminoglycans, proteoglycans, and glycoproteins-most notably fibronectin. Thus, various components, purified from matrix using methods known to those skilled in the art, and particularly the RGD fraction of fibronectin, laminin, and proteoglycans, can be combined in various concentrations to produce a gel-like "synthetic membrane" which is a functional equivalent of extracellular matrix (as well as being a derivative of extracellular matrix) for the coating process of the present invention. Additionally, several polymers have been used on which to seed cells for enhanced attachment, that may also function equivalently in the coating process of the present invention.

It should be understood that the embodiments and the examples of the present invention, as described herein, are for purposes of illustration only, and not limitation, and any changes or modifications as will become apparent to one of ordinary skill in the art from the foregoing description and accompanying figure are intended to be included within the scope of the appended claims and the equivalents thereof.

What is claimed is:

1. A method of treating lumenal surfaces in the vasculature of a tissue or organ to be grafted, said method comprises the steps of:

(a) removing the organ or tissue to be grafted from the donor, (b) perfusing or infusing the organ or tissue with a preservation solution, (c) coating the vascular endothelial cells lining the lumen of the blood vessels within the vasculature of the organ or tissue to be grafted with a solution comprising a solubilized or partially polymerized extracellular matrix preparation derived from endothelial cells in a concentration sufficient to render the lumenal surfaces of the organ or tissue nonthrombogenic, and substantially nonimmunogenic as determined by at least a 99% inhibition in a cell-mediated reaction to the treated graft as compared to that of an untreated graft, to a recipient of said graft.

2. The method according to claim 1, further comprising d) allowing the coating formed by the extracellular matrix preparation to serve as a surface for re-endothelialization by vascular endothelial cells autologous with the recipient of said graft, wherein the vascular endothelial cells which re-endothelialize the extracellular matrix coating are an additional barrier between the recipient's immune system and the donor's vascular endothelial cells coated by the extracellular matrix.

3. The method of claim 1, wherein steps b) and c) are performed in warm preservation at temperatures in a range of about 22° C. to 35° C. which supports metabolism in the organ or tissue for at least 18 hours during which time period the lumenal surfaces of the organ or tissue are coated.

4. The method according to claim 2, wherein in step d), the vascular endothelial cells which re-endothelialize onto the coating formed by the extracellular matrix preparation are autologous with the recipient's vascular endothelial cells.

5. The method according to claim 4, wherein in step d) occurs in vivo after grafting the treated organ or tissue into the recipient.

6. The method according to claim 4, wherein step d) occurs prior to grafting the treated organ or tissue by in vitro perfusion or infusion of said vascular endothelial cells into the treated organ or tissue.

7. The method of claim 1, wherein the extracellular matrix preparation is of human corneal endothelial cell origin.

* * * * *